United States Patent

Feinbloom et al.

[19]

[11] Patent Number: 6,007,035
[45] Date of Patent: Dec. 28, 1999

[54] CLIP-ON BRACKET ASSEMBLY USING SPRING WASHERS FOR ATTACHING TO FIXTURES

[75] Inventors: Richard E. Feinbloom, New York; Peter J. Murphy, Port Washington, both of N.Y.

[73] Assignee: Designs for Vision, Inc., Ronkonkoma, N.Y.

[21] Appl. No.: 08/985,496

[22] Filed: Dec. 5, 1997

[51] Int. Cl.[6] .................................................. A47B 96/06
[52] U.S. Cl. .............................. 248/229.16; 248/231.81; 248/689
[58] Field of Search .................... 248/231.71, 231.81, 248/291.1, 682, 689, 902, 229.14, 229.16, 231.61, 231.85; 24/3.5, 3.7, 3.8, 3.11, 3.12, 457; 2/13; 362/206

[56] References Cited

U.S. PATENT DOCUMENTS

| | | | |
|---|---|---|---|
| 1,510,805 | 10/1924 | Smith | 24/457 |
| 3,150,380 | 9/1964 | Porcello | 2/13 |
| 3,955,884 | 5/1976 | Del Pesco, Sr. | 350/248 |
| 4,193,173 | 3/1980 | Lorenz | 24/457 |
| 4,413,379 | 11/1983 | Evans | 24/3.11 |
| 4,878,641 | 11/1989 | Vogt | 24/457 |
| 5,052,793 | 10/1991 | Lapp et al. | 248/231.71 |
| 5,267,130 | 11/1993 | Maglica et al. | 362/206 |
| 5,412,812 | 5/1995 | Gatchalin | 2/10 |
| 5,541,767 | 7/1996 | Murphy et al. | 359/399 |
| 5,720,456 | 2/1998 | Szybura | 248/231.81 |

*Primary Examiner*—Derek J. Berger
*Assistant Examiner*—Gwendolyn Baxter
*Attorney, Agent, or Firm*—Arthur L. Plevy

[57] ABSTRACT

There is disclosed a clip-on bracket assembly for detachably coupling to a first fixture comprising a first bracket member having an inner surface and an outer surface, the inner surface including a first planar surface portion and a second arcuate portion. A second bracket member substantially parallel to the first bracket member has an inner surface and an outer surface. The second member inner surface includes a first planar portion and a second arcuate portion wherein the first planar portions of the first and second members are fixedly coupled by means of an at least one spring washer. The second arcuate portions of the respective members are in parallel arrangement defining a gap therebetween for receiving and securing the fixture, where the first arcuate portion is springably movable with respect to the second arcuate portion to accommodate fixtures of varying widths.

17 Claims, 4 Drawing Sheets

6,007,035

CLIP-ON BRACKET ASSEMBLY USING SPRING WASHERS FOR ATTACHING TO FIXTURES

FIELD OF THE INVENTION

The invention relates to bracket assemblies, and more particularly, to bracket assemblies employing spring washers to springably attach to fixtures.

BACKGROUND OF THE INVENTION

A number of devices currently exist in the prior art for securing objects to eyeglasses. For example, there are many well-known clip-on devices for securing such items as sun visors, ornamental fixtures, as well as connecting eyeglass frames together at a bridge area to form a single structure. Many clip-on devices utilize set screws for securing for example, a fixture to the frame of an eyeglass. Such a clipping device, however, is very time consuming and labor intensive, requiring the user to, either manually or with the aid of a screwdriver, screw in the set screw in order to secure the clip to the frame.

In the medical field, for example, health care professionals including surgeons, as well as other health care providers who typically treat patients, often require a light for illuminating a particular area of a patient's body during examination. Mounting a light source to the frame of one's glasses thus permits the hands to remain free to perform more important functions other than holding a light source, including actively assisting in the medical treatment. However, because of the time factor and difficulty in assembling and removing a clippable device such as a light source to an eyeglass frame, applications such as these have had little success. Accordingly, a clip-on device which secures to the frame of a set of eyeglasses that is easy to install and remove, yet sufficiently lightweight and secure, is greatly desired.

SUMMARY OF THE INVENTION

The present invention provides a clip-on bracket assembly for detachably coupling to a first fixture comprising: a first bracket member having an inner surface and an outer surface, said inner surface including a first planar surface portion and a second arcuate portion, a second bracket member including a bracket portion substantially parallel to said first bracket member having an inner surface and an outer surface, said second member bracket inner surface including a first planar portion and a second arcuate portion wherein said first planar portions of said first and second members are fixedly coupled by means of an at least one spring washer, wherein said second arcuate portions of said respective members are in parallel arrangement defining a gap therebetween for receiving said fixture and securing thereto, wherein said first arcuate portion is springably movable with respect to said second arcuate portion to accommodate fixtures of varying widths.

BRIEF DESCRIPTION OF THE DRAWINGS

The invention is to be explained in more detail below based on embodiments, depicted in the following figures where.

DETAILED DESCRIPTION OF THE INVENTION

Figure 1:
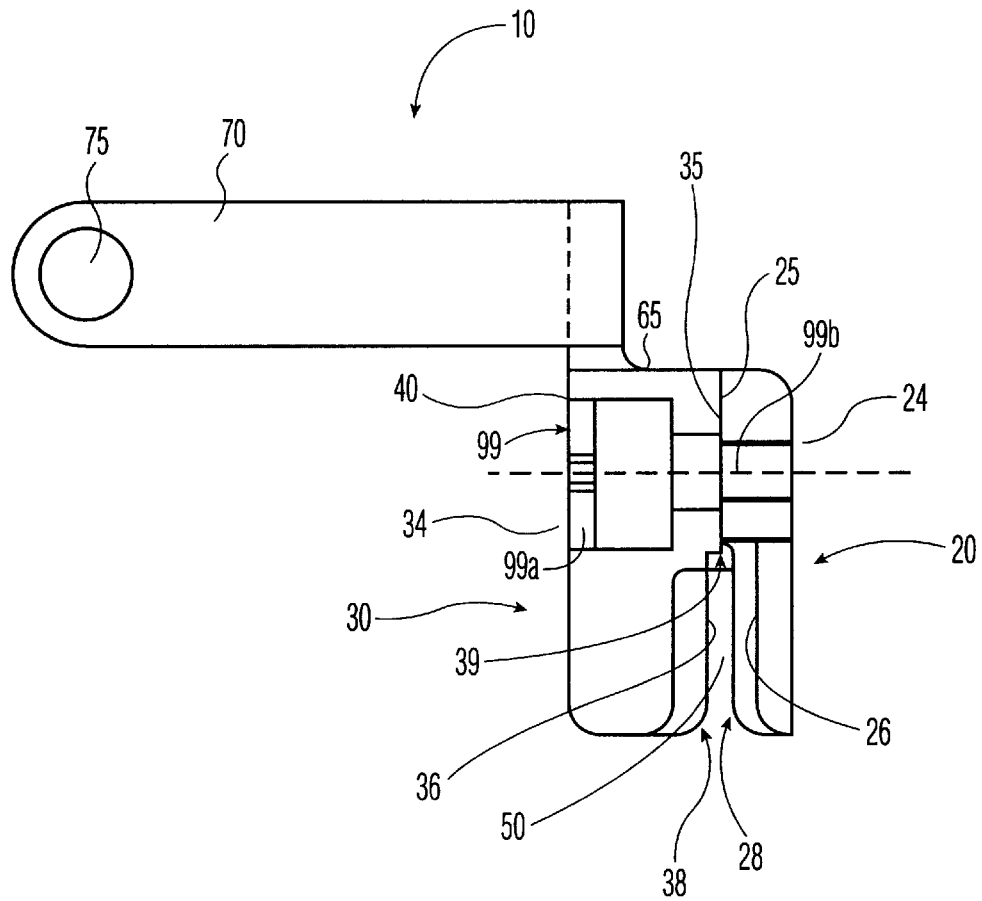
FIG. 1 is a cross sectional side view of the bracket assembly according to an embodiment of the invention.
Figure 2:
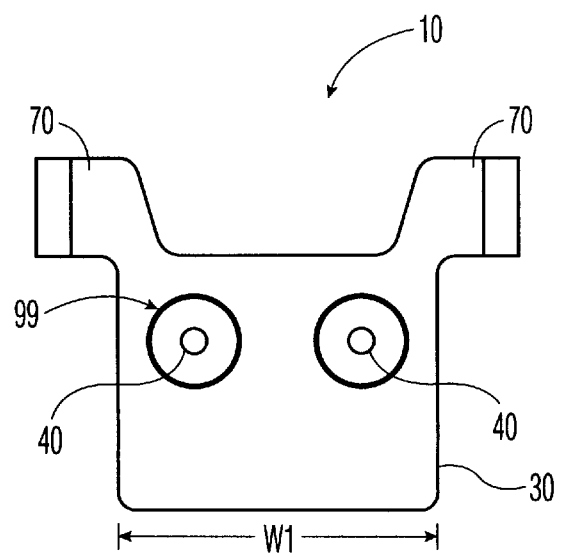
FIG. 2 is a front view of the bracket assembly according to an embodiment of the invention.

Referring now to FIG. 1, there is shown a cross-sectional side view of the clip-on bracket assembly 10 according to the invention. The bracket assembly 10 comprises a first bracket member 20 coupled to a second bracket member 30 by means of a spring washer 40 and bolt 99. In the preferred embodiment, and as more easily seen in FIG. 2 (front view of bracket assembly), two spring washers are used to fixably couple the first and second bracket members (20,30) to one another bolt using bolt 99. Note that throughout all references to the drawings, like parts are indicated by like reference numerals. The first bracket member 20 is a monolithic structure including a substantially planar outer surface 24 and an inner surface 28 having a first planar portion 25 and a first arcuate portion 26. The second bracket member 30 comprises a substantially planar outer surface 34 and an inner surface 38 which includes a planar portion 35 and an arcuate portion 36. Second bracket member 30 further comprises an at least one arm portion 70 integrally extending from the top surface 65 for attaching to and securing a fixture such as a light source. Arcuate portions 26 and 36 of respective bracket members 20 and 30 are arranged in parallel to one another, defining a cavity 50 formed therebetween.

Figure 4:
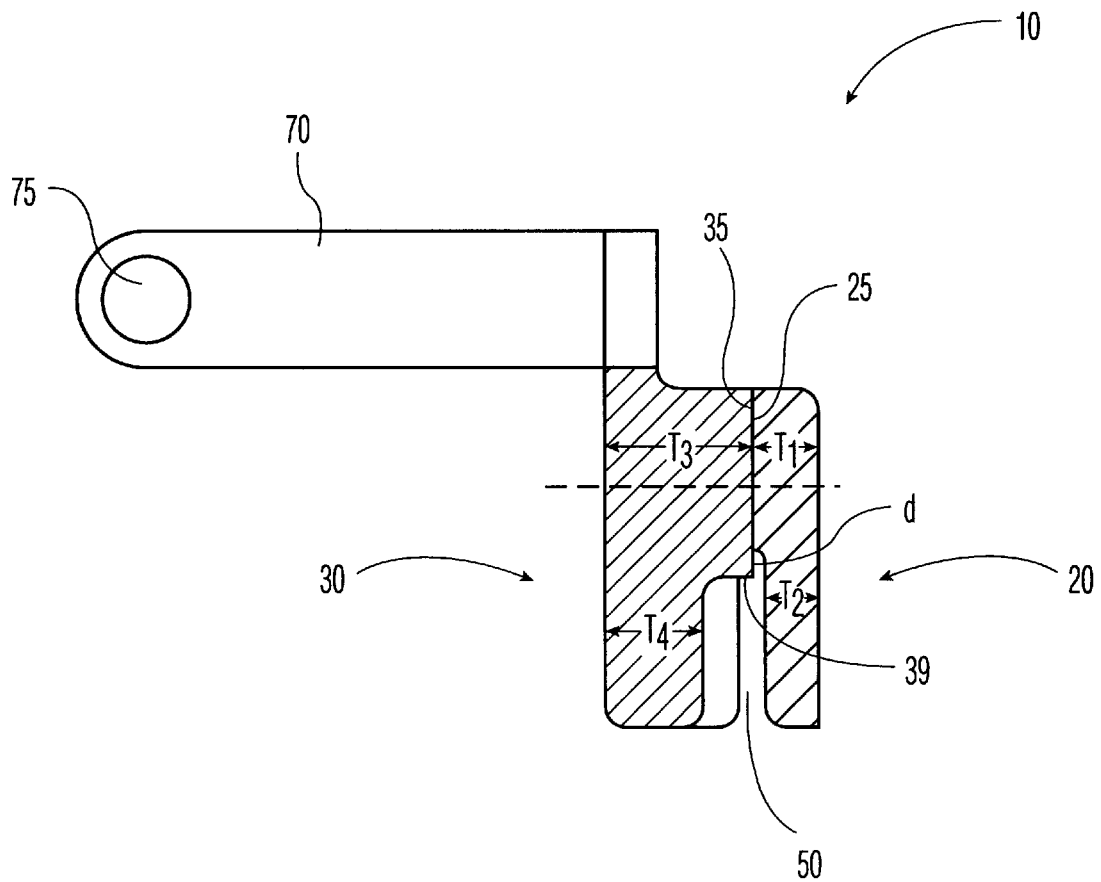
FIG. 4 is a side view of the bracket assembly according to an embodiment of the invention.
Figure 7:
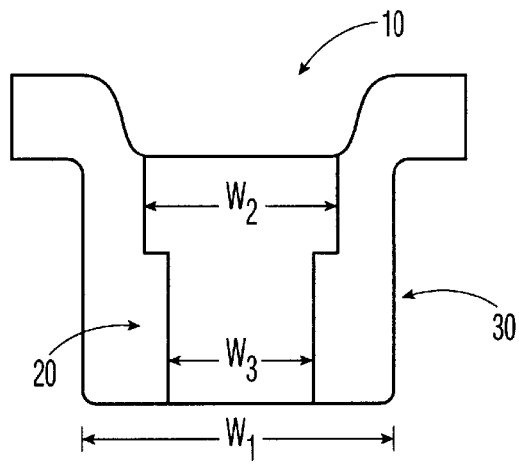
FIG. 7 is a back view of the bracket assembly according to an embodiment of the invention.

As seen in FIG. 4, the first bracket member 20 has a substantially uniform thickness T1 associated with the first planar portion 25. A second portion of varying thickness T2 corresponds to the first arcuate portion of the first bracket member 20, where the thickness T2 is less than the thickness T1 associated with the first planar portion. Similarly, bracket member 30 has a first portion associated with the planar portion 35 having a substantially uniform thickness T3. A second portion of bracket member 30 associated with the arcuate portion 36 has a variable thickness T4 which in the preferred embodiment is less than thickness T3. Preferably, the thickness T3 associated with planar portion 35 is greater than that associated with planar portion 25. Note also that variable thickness T4, at its minimum, also exceeds thickness T1. As shown in FIG. 7, the width w1 associated with bracket member 30 is substantially uniform while member 20 comprises a first smaller width w2 (relative to w1) associated with planar portion 25 and a second width w3 associated with arcuate portion 26, which is smaller than either w1 or w2. In this manner, bracket member 30 provides a strong base serving to anchor the more flexible member 20, while at the same time serving to minimize the size and weight requirements of the overall assembly. The structural dimensions of member 20 relative to member 30 also serve, in the case of an assembly affixed to the bridge of a pair of eyeglasses, to minimize surface area contact with the forehead of a wearer.

Figure 3:
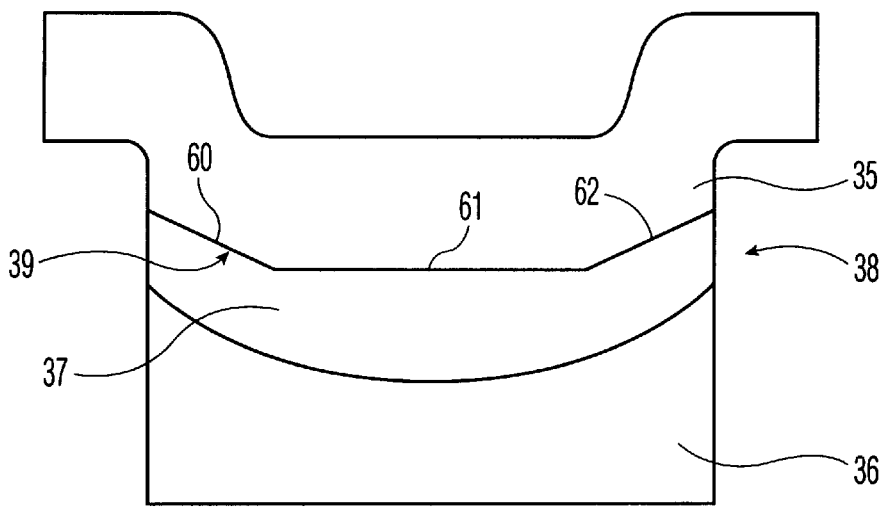
FIG. 3 is a view of the inner surface of the second bracket member of the bracket assembly according to an embodiment of the invention.

Referring now to FIG. 3, there is shown a view of inner surface 38. As shown in FIG. 3, a channel 37 is formed in surface 38 between portions 35 and 36 which separates the two segments. Formation of the channel 37 between the two segments results in a chamfered ledge 39 being formed on the underside of portion 35 which extends transversely beyond arcuate portion 36 as best seen in FIG. 1. Chamfered ledge 39 comprises angled portions 60 and 62 extending from either side of bracket member portion 30 and coupled together via horizontal ledge portion 61 on which a fixture inserted into cavity 50 engages to span the width of bracket 31, thus enabling the bracket assembly to rest on the fixture via the ledge 39. The inner surface portions of each member are urged towards one another by means of the spring washers to engage and secure opposite sides of the fixture within the cavity. The bracket assembly detaches from the fixture via exertion of a relatively small force in a longitudinal direction relative to members 20 and 30 to extract the fixture from the assembly.

Figure 5:
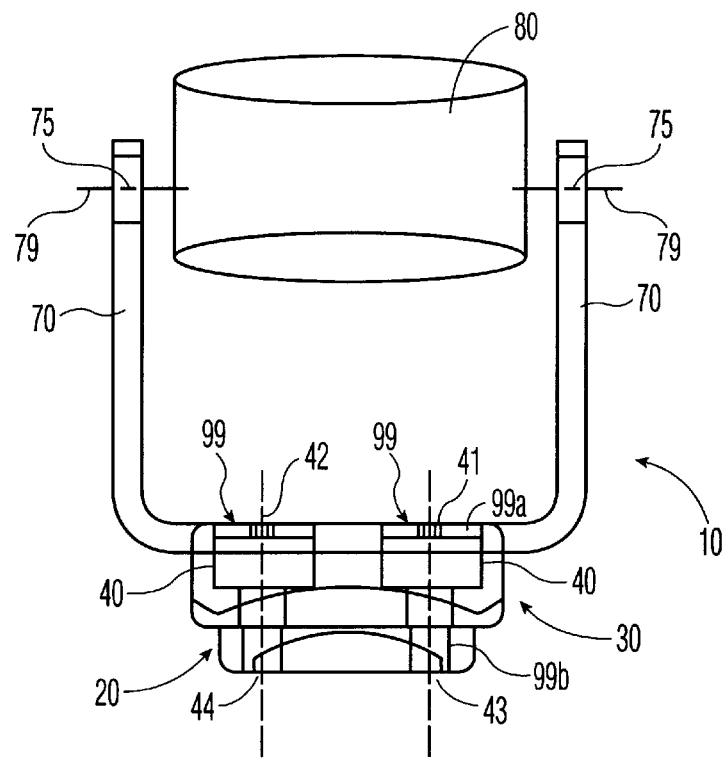
FIG. 5 is a top view of the bracket assembly according to an embodiment of the invention.

As previously stated, FIG. 4 shows a side view of the bracket assembly 10. As shown in FIG. 4, planar portion 35 extends a distance beyond first planar portion 25 so that the gap 50 and ledge 39 combination can accommodate, engage, and secure a fixture (not shown). In the preferred embodiment, bore holes 41 and 42 extend through bracket member 30 and bore holes 43 and 44 extending through bracket member 20 are aligned to receive the two bolts 99 and corresponding two spring washers 40 as shown in FIG. 5. As can be seen in FIG. 5 (and in FIG. 1) bolt 99 includes head portion 99A and body portion 99B extending through bracket members 30 and 20, wherein spring washers 40 are disposed between the head portion 99A and body portion 99B. Each of the spring washers 40 operate to urge bracket member 20 toward bracket member 30. When a fixture such as the bridge of an eyeglass frame is inserted into the cavity 50, the bridge frame having a width slightly greater than the cavity width, the resilient bracket member 20 is pivotally displaced a distance relative to bracket member 30 to enlarge the cavity so as to accommodate the frame. Note that the first arcuate portion 26 is pivotally displaced from the arcuate portion 36 by the engaging fixture while the remaining portion of member 20, namely first planar portion 25, remains fixably coupled via the bolt and corresponding spring washer to the planar portion 35. In this manner, the bracket assembly can accommodate varying widths exceeding that of the cavity 50, because the tension from the spring washers 40 apply a force which urges member 20 toward bracket member 30, thus securing the fixture or bridge frame into position.

Figure 6:
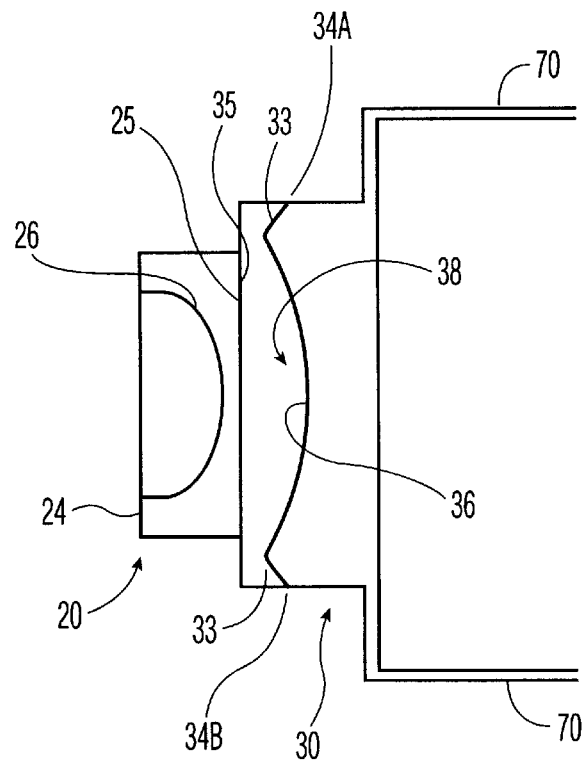
FIG. 6 is a bottom view of the bracket assembly according to an embodiment of the invention.

FIG. 6 shows a bottom view of the bracket assembly. As seen in FIG. 6, bracket member portion 30 includes Chamfered edge portion 33 formed on inner surface 38 at each of the edges (34A and 34B) of bracket member 30 and which extend longitudinally to end at channel 37 (see FIG. 3). Arcuate portion 36 extends between and couples each of Chamfered edge portions 33. The chamfered edge portions thus permit a more planar surface for engaging and hence, securing a fixture as it slides within the cavity 50.

Figure 8A:
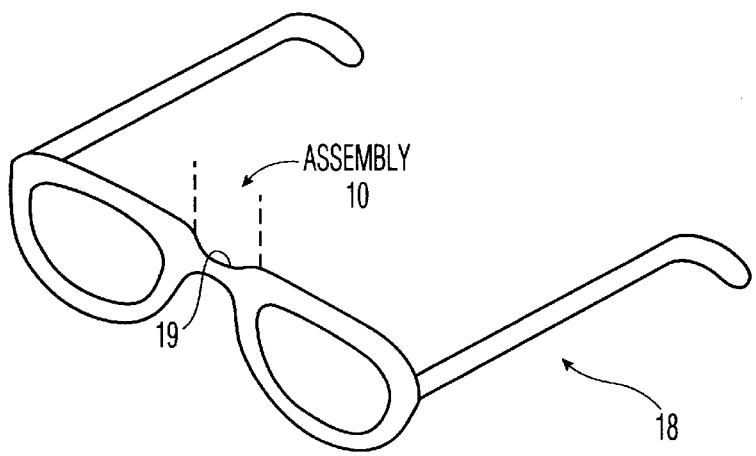
FIGS. 8A and 8B are perspective and side views respectively, of the bracket assembly connection with a pair of eyeglasses according to an embodiment of the invention.
Figure 8B:
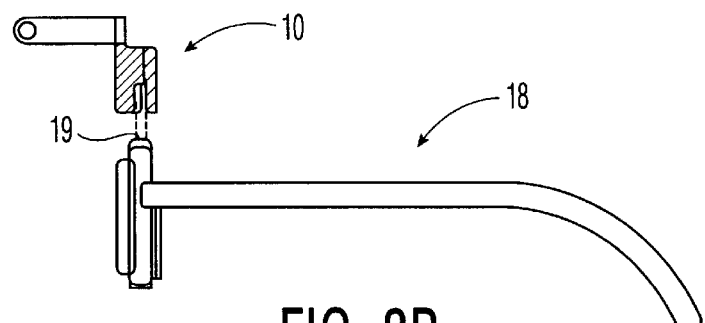

As shown in FIGS. 1–6, and clearly in FIG. 1, bracket member 30 further includes arm member 70 extruding from a top surface 65 for attaching to a second fixture 80 (see FIG. 5) such as a light source. As shown in FIG. 1, arm member 70 includes a hole 75 adaptable for receiving a set screw 79 or any other means for attaching the arm to the second fixture. In the preferred embodiment, and as clearly shown in FIG. 5, first and second arm members 75 extend from opposite ends of top surface 65 of bracket member 30 and are oriented substantially perpendicular to the parallel bracket member portions of bracket members 30 and 20. The bracket arms 70 extend in a direction opposite that of bracket member 20. The dual arm members thus permit a device or fixture 80 such as a light source to be secured to the bracket assembly. As can be seen from FIGS. 8A–B, the bracket assembly 10 may then be fitted over the bridge area 19 of an eyeglass frame 18 for example, by forcing the bridge area of the frame between the two parallel positioned inner surface portions of members 20 and 30, thus pivotally displacing inner surface arcuate portion 26 until the top of the bridge of the eyeglass frame engages ledge 39 of bracket member 30. The urging of the dual spring washers 40 attract arcuate portion 26 toward arcuate portion 36 of member 30, thereby firmly securing the clip to the bridge of the eyeglass frame. The second fixture, such as a light source, is thus mounted via arms 70 of the clip to the eyeglass frame and may be positioned in any number of axial directions by means of the arm members and set screws or other securing means, including but not limited to bolts and rivets among others. In the preferred embodiment, the first bracket member 20, which is monolithically structured, is made of a resilient material, such as plastic, to assist in adapting to the width of the first fixture. Similarly, the second member 30 is also monolithically structured and made of a resilient lightweight material such as plastic in order to accommodate any variations in width, as well as to provide a lightweight, flexible, clip-on device.

While there have been shown preferred embodiments of the present invention, those skilled in the art will further appreciate that the present invention may be embodied in other specific forms without departing from the spirit or central attributes thereof. Accordingly, all such variations and modifications are intended to be within the scope of this invention as defined by the appended claims.

What is claimed is:

1. A clip-on bracket assembly for detachably coupling to a first fixture comprising;

a first bracket member having an inner surface and an outer planar surface, said inner surface including a first planar portion and a second arcuate portion located opposite said outer planar surface, a second bracket member substantially parallel to said first bracket member and having an inner surface and an outer planar surface, said second bracket member inner surface including a first planar portion and a second arcuate portion opposite said outer planar surface of said second bracket member wherein said first planar portions of said inner surfaces of said first and second bracket members are fixedly coupled to one another by means of an at least one bolt and spring washer, wherein said second arcuate portion of said second bracket member inner surface is in parallel arrangement with said second arcuate portion of said first bracket member inner surface defining a gap therebetween for receiving said first fixture and securing thereto, wherein said second arcuate portion associated with said first bracket member is springably movable with respect to said second arcuate portion of said second bracket member to accommodate fixtures of varying widths wherein said second member bracket further includes a channel formed within said inner surface between said second arcuate portion and said first planar portion of said second member bracket defining a ledge, said ledge for engaging said first fixture for preventing further insertion of said first fixture into said gap.

2. The bracket assembly of claim 1, wherein said second bracket member further includes an at least one arm member for adjustably coupling to a second fixture to permit motion of said second fixture in at least one axis.

3. The bracket assembly according to claim 2, wherein two arm members integrally extend from a top surface of said second bracket member for adjustably attaching to said second fixture to permit rotation along a single axis.

4. The bracket assembly according to claim 3, further comprising securing means for adjustable connecting said first and second arm members to said second fixture.

5. The bracket assembly according to claim 4, wherein said securing means are set screws.

6. The bracket assembly of claim 2, wherein said second fixture is an illumination device.

7. The bracket assembly according to claim 1, wherein said second member bracket has a substantially uniform width.

8. The bracket assembly according to claim 1, wherein said ledge is chamfered.

9. The bracket assembly of claim 1, wherein said first fixture is a pair of eyeglasses.

10. The bracket assembly according to claim 9, wherein said arcuate portion of said first member and said arcuate portion of said second member defining said gap are adapted to receive and fixably couple a bridge portion of said eyeglasses to said bracket assembly.

11. A clip-on bracket assembly for detachably coupling to a pair of eyeglasses comprising:

a first bracket member having an inner surface and an outer planar surface, said inner surface including a first planar portion and a second arcuate portion opposite said outer planar surface;

a second bracket member substantially parallel to said first bracket member and having an inner surface and an outer planar surface, said second bracket member inner surface including a first planar portion and a second arcuate portion opposite said outer planar of said second bracket member wherein said first planar portions of said inner surfaces of said first and second members are fixedly coupled to and in contact engagement with one another by means of an at least one bolt and spring washer so as to form a ledge at an interior of said bracket assembly, wherein said second arcuate portion of said second bracket member inner surface is in parallel arrangement with said second arcuate portion of said first bracket member inner surface defining a gap therebetween which terminates at said ledge for receiving said eyeglasses and securing thereto, wherein said second arcuate portion associated with said first bracket member is springably movable with respect to said second arcuate portion associated with said second bracket member to accommodate eyeglass frames of varying widths.

12. The bracket assembly of claim 11, wherein said second bracket member further includes an at least one arm member adjustably coupled to a second fixture to permit motion of said second fixture in at least one axis.

13. The bracket assembly of claim 12, wherein said second fixture is a light source.

14. The bracket assembly of claim 11, wherein said ledge is chamfered.

15. The bracket assembly of claim 11, wherein said first bracket member has a first thickness (T1) associated with said first planar portion and a variable thickness (T2) less than the first thickness (T1) associated with said second arcuate portion; and said second bracket member bracket portion has a third thickness (T3) associated with said planar portion and a variable thickness (T4) less than the third thickness (T3) associated with said arcuate portion.

16. The bracket assembly of claim 15, wherein the third thickness (T3) is greater than the first thickness (T1).

17. The bracket assembly of claim 11, wherein said first bracket member has a first width (w1) associated with said first planar portion and a second width (w2) less than the first width (w1) associated with said second arcuate portion; and said second bracket member has a substantially uniform width (w3) greater than the first width (w1).

\* \* \* \* \*